US00PP35539P2

(12) United States Plant Patent
Wu et al.

(10) Patent No.: US PP35,539 P2
(45) Date of Patent: Dec. 12, 2023

(54) BERMUDAGRASS CULTIVAR 'OKC3920'

(50) Latin Name: ***Cynodon dactylon* (L.) Pers. X *C. transvaalensis* Burtt-Davy**
Varietal Denomination: OKC3920

(71) Applicant: THE BOARD OF REGENTS FOR THE OKLAHOMA AGRICULTURAL AND MECHANICAL COLLEGES, Stillwater, OK (US)

(72) Inventors: Yanqi Wu, Stillwater, OK (US); Justin Q. Moss, Stillwater, OK (US); Dennis Loren Martin, Stillwater, OK (US); Nathan Walker, Guthrie, OK (US); Charles H. Fontanier, Stillwater, OK (US)

(73) Assignee: THE BOARD OF REGENTS FOR THE OKLAHOMA AGRICULTURAL AND MECHANICAL COLLEGES, Stillwater, OK (US)

( * ) Notice: Subject to any disclaimer, the term of this patent is extended or adjusted under 35 U.S.C. 154(b) by 0 days.

(21) Appl. No.: 17/803,804

(22) Filed: Nov. 29, 2022

(51) Int. Cl.
*A01H 5/12* (2018.01)
*A01H 6/46* (2018.01)

(52) U.S. Cl.
USPC ..... Plt./389

(58) Field of Classification Search
USPC ..... Plt./389
CPC ... A01H 5/12; A01H 5/00; A01H 6/46; A01H 6/4612
See application file for complete search history.

(56) References Cited

U.S. PATENT DOCUMENTS

| | | | |
|---|---|---|---|
| PP9,888 | P | 5/1997 | Brown et al. |
| PP11,163 | P | 12/1999 | Hanna |
| PP12,084 | P2 | 9/2001 | Kaerwer et al. |
| PP26,638 | P3 | 4/2016 | Chapman |
| PP31,695 | P3 | 4/2020 | Wu et al. |

*Primary Examiner* — June Hwu
(74) *Attorney, Agent, or Firm* — McKee, Voorhees & Sease, PLC

(57) ABSTRACT

'OKC3920' is disclosed herein as a new clonally propagated F1 hybrid bermudagrass cultivar with improved freeze tolerance, tolerance to low mowing heights, early spring green up, and high turfgrass quality.

1 Drawing Sheet

Botanical designation:
Genus and species: *Cynodon dactylon* (L.) Pers. X *C. transvaalensis* Burtt-Davy.
Cultivar denomination: The new plant has the cultivar denomination 'OKC3920'.

SUMMARY

This disclosure relates to a new and distinct cultivar of bermudagrass designated 'OKC3920' and botanically known as *C. transvaalensis* Burtt-Davy x *C. dactylon* Persoon. 'OKC3920' is a turf-type, clonally propagated, F1 bermudagrass hybrid characterized by improved cold hardiness, tolerance to low mowing heights, early spring green up, dark green color, and high potential for use on golf putting greens.

BRIEF DESCRIPTION OF DRAWINGS

FIG. 1 is a photograph is a photograph comparing stems and leaves of 'OKC3920', 'Tahoma 31', 'OKC0805', 'OKC0920', 'TifEagle', 'Tifdwarf', '11x2', '19x19', '15x9', and '12x3' grown in an established, replicated nursery in Stillwater, Oklahoma in 2022.

DETAILED BOTANICAL DESCRIPTION

The following is a detailed botanical description of the new cultivar of bermudagrass, its flowers, foliage etc. as based on two years of continuous observations of specimens grown in field conditions in various locations throughout Oklahoma, Indiana, Florida, Mississippi, New Mexico, Georgia, Missouri, Texas, and California.

ORIGIN AND HISTORY

'OKC3920' is a clonally propagated F1 hybrid from a cross of *C. dactylon* var. *dactylon* Oklahoma State University (OSU) selection '17x14' (2n=4x=36) x *C. transvaalensis* OSU selection '1115' (2n=2x=18). '17x14' (unpatented) was one genotype in a population of common bermudagrass, which survived two winters in a space-planted nursery established in the summer of 2009 in Champaign, Illinois. The genotype '17x14' was selected from a replicated nursery established in Stillwater, Oklahoma in 2011 due to its early spring green up and short internodes. '1115' (unpatented) is a fine-textured, dark-green African bermudagrass genotype that was selected in 2011 from a nursery established in Stillwater, Oklahoma.

'OKC3920' may be distinguished from its parents by the following characteristics: 'OKC3920' is sexually sterile but the two parents are sexually fertile. 'OKC3920' has leaf blades finer than '17x14' but coarser than '1115'.

A small crossing plot was established by planting clonal plants of the two parents in close proximity in Stillwater, Oklahoma on Jul. 29, 2013. Seed was hand-harvested from the parents in the crossing block in the summer of 2014. 372 seedlings from the harvested seed of this cross, along with seedlings from other crosses, were transplanted to a space-planted selection nursery of 830 plants in Stillwater, Oklahoma on Jun. 23, 2015. In the spring of 2017, 'OKC3920' was selected from the nursery along with 16 other experimental selections and four commercial cultivars 'TifEagle' (U.S. Plant Pat. No. 11,163), 'Champion Dwarf' (U.S. Plant Pat. No. 9,888), 'C-7' (U.S. Plant Pat. No. 26,638) [source material Sunday™ bermudagrass], and 'P18' (U.S. Plant Pat. No. 12,084) [source material MiniVerde® bermudagrass]. These selections were used to establish a mowing test in Stillwater, Oklahoma on Jun. 22, 2017. In the mowing test, 'OKC3920' performed well at the cutting height of 3.2 mm in the summer of 2018. In 2019, 'OKC3920' was advanced to the 2019 National Turfgrass Evaluation Program (NTEP) National Warm-season Greens Test (NTEP, 2019).

'OKC3920' has been asexually reproduced in Stillwater, OK using sprigs, stolons, or shoots of the original plant. The cultivar is stable and reproduces true to type in successive generations of asexual reproduction.

MORPHOLOGICAL CHARACTERISTICS AND PERFORMANCE

'OKC3920' forms a dense turf through its growth of stolons, rhizomes, and shoots. It is a perennial grass with vigorous growth in the summer and dormancy in the winter. As it is sexually sterile, its reproduction is solely clonal or vegetative.

'OKC3920' has a foliage color of RHS 143A. The cultivar has fine and deep rhizomes with pale yellow color (RHS 162D), and fine stolons of color RHS 143A. Both upper leaf blade surfaces and lower leaf blade surfaces have no hairs. Leaf sheaths have some fine hairs as well. Leaf sheaths and culm have a color of RHS 143A. Collars are whitish (RHS 157D) and narrow. When mature, glumes, lemmas, and paleas are brown with purple color. Leaf blade color in the winter is RHS 8D.

Respective leaf blade width and length are 1.1 mm and 14.6 mm on average. The average internode length and diameter of stolon are 4.5 mm and 0.47 mm. Leaf sheath is 1.0 mm in length. Ligule is 1-2 mm long. Each spikelet is 2.5 mm long. Peduncle is 30 mm long. Plant culms are 40 mm long.

'OKC3920' has a flat, linear leaf blade with a sharp apex. The outside surface of its leaf sheath is soft, shiny without hairs. Its leaf sheath is overlapped at the base but split toward the blade. Its leaf texture is soft. It has a smooth leaf blade margin. Its ligule is membranous with short hairs. Its auricle is absent with white hairs (about 1-2 mm in length). Its collar is continuous but narrow. One dormant bud is present and covered by a leaf sheath on a mature node. Leaves are rolled in the bud.

Each inflorescence consists of 2-3 racemes in one whorl. There are 18 spikelets on each raceme. Each spikelet contains one floret. It flowers in June in Stillwater, OK. 'OKC3920' has yellowish anthers and purple feathery stigmas. 'OKC3920' is sterile and does not produce seed.

'OKC3920' has been evaluated in Stillwater, Oklahoma and more extensively in the 2019 NTEP National Warm-season Greens Test. This NTEP test provided data from 9 locations in 2019 and 2020. 'Tifdwarf' (unpatented), 'TifEagle', and 'P18' were comparative standard cultivars in the national test. The major performance characteristics of 'OKC3920' are described as follows.

Establishment Rate: The NTEP test establishment rate data for 2019 indicates that 'OKC3920' has similar or faster establishment ratings as compared to the standard cultivars. In Indiana, Florida, and Mississippi, 'OKC3920' had establishment rates similar to 'P18', 'TifEagle', and 'Tifdwarf'. In Oklahoma, 'OKC3920' established in a similar rate to 'TifEagle', but faster than 'Tifdwarf' and 'P18'. In New Mexico, 'OKC3920' had an establishment rate similar to 'TifEagle' and 'Tifdwarf', but faster than 'P18'. In Georgia, the establishment rate of 'OKC3920' was similar to that of 'P18', but quicker than that of 'TifEagle' and 'Tifdwarf'.

Turfgrass Quality (TQ): The NTEP TQ was visually evaluated using a scale of 1 (least quality) to 9 (maximum quality). When TQ was averaged over all eight locations of the NTEP test, 'OKC3920' was in the top performing statistical group among bermudagrass entries. In Missouri, 'OKC3920' had a quality rating (6.9) better than 'Tifdwarf' (5.3) and 'P18' (4.8), but was not different from 'TifEagle' (6.1). In the other seven locations (Georgia, Florida, Mississippi, Indiana, Texas, New Mexico, and California), turfgrass quality ratings of 'OKC3920' were not different from that of 'TifEagle', 'Tifdwarf', and 'P18'.

Ball Rolling Measurements: The 2019 NTEP test reported ball roll distances collected in California, Mississippi, and New Mexico in 2020. In California, 'OKC3920' had a ball roll distance of 70 inches, which was statistically not different from that of 'P18' (85.5"), but shorter than that of 'TifEagle' (90.7") and 'Tifdwarf' (92.0"). In Mississippi, the ball roll distance of 'OKC3920' (80.0") was not different from 'TifEagle' (87.5"), 'Tifdwarf' (86.3"), and 'P18' (87.7"). In New Mexico, 'OKC3920' had a ball roll distance (116.7") similar to 'Tifdwarf' (113.8"), 'TifEagle' (119.8"), and 'P18' (124.0").

Spring Greenup: Spring greenup ratings (scale 1-9, 9=maximum greenup) were visually assessed for the earliness of spring regrowth from established plots in the NTEP trial. Spring greenup ratings reflect the comparative winter hardiness of entries as compared to standard cultivars. The 2020 spring greenup rating of 'OKC3920' in the NTEP test averaged over four locations (California, Missouri, Mississippi, and New Mexico) was 7.2, statistically higher than that of 'TifEagle' (6.4), 'Tifdwarf' (5.5), and 'P18' (5.3).

Freeze Tolerance: When ultradwarf bermudagrass cultivars (e.g., 'TifEagle', 'Champion Dwarf', and 'P18') are grown for putting greens on golf courses in the US transition zone, winterkill is a major concern. Development of new bermudagrass cultivars with improved freeze tolerance is thus needed. An experiment including 'OKC3920', experimental genotype 'OKC0920', and two commercial cultivars (Champion Dwarf as a susceptible standard and 'OKC 1131' (U.S. Plant Pat. No. 31,695, source material Tahoma 31® bermudagrass) as a tolerant standard) was conducted to quantify freeze tolerance. The results indicated that 'OKC3920' had a level of freeze tolerance similar to 'OKC 1131' (one of the most cold hardy turf bermudagrass cultivars commercially available at the time of testing), but significantly better than 'Champion Dwarf' (Table 1).

TABLE 1

Lethal temperatures resulting in 50% survival ($LT_{50}$) of four bermudagrass genotypes when exposed to temperatures ranging from −4 to −14° C. under controlled environment conditions. Same letter in same column indicates no statistical difference.

| Genotype | $LT_{50}$ (° C.) |
|---|---|
| 'Champion Dwarf' | −5.2 a |
| 'OKC0920' | −7.1b |
| 'OKC3920' | −8.1.c |
| 'OKC 1131' | −8.8.c |
| LSD (0.05) | 0.8 |

Winterkill: The NTEP winterkill scale ranged from 0 for no winterkill to 99% as complete kill. The NTEP 2020 winterkill data for bermudagrass entries at West Lafayette, Indiana, indicated that 'OKC3920' had the least winterkill rate (2.7%), although the value was not statistically lower than that of 'Tifdwarf' (7.0%), 'TifEagle' (12.7%), and 'P18' (17.7%).

Genetic Color: Genetic color data was collected when the grasses were grown actively without stress and were evaluated using a scale from 1 (light green) to 9 (maximum dark green color). 'OKC3920' has a dark green leaf color. In the NTEP test, the 2020 data indicated that the genetic color rating of 'OKC3920' (7.2) was statistically higher than that of 'TifEagle' (6.7) and 'Tifdwarf' (6.4) but not different from 'P18' (7.1).

Leaf Texture: 'OKC3920' has relatively lengthy, fine-textured leaf blades. In 2020, the NTEP test (scale 1-9, 9=maximum fine leaf texture) data indicated that the overall leaf texture rating of 'OKC3920' (7.4) was statistically the same as that of 'P18' (7.1), but finer than 'Tifdwarf' (6.9) and 'TifEagle' (6.9).

Density: Density is the overall visual effect of the number of living plants per unit area of turfgrass canopy and is evaluated on a 1-9 scale, with 9=maximum density for the species. The 2020 NTEP test reported that in California, spring density of 'OKC3920' (5.3) was lower than that of 'TifEagle' (6.3), but not different from 'P18' (5.7) and 'Tifdwarf' (5.7), summer density and fall density of 'OKC3920' was not different from that of either of the three standard cultivars. In Florida, 'OKC3920''s fall density rating (6.7) was better than 'TifEagle' (5.3) and 'Tifdwarf' (5.0), but not different from 'P18' (5.7).

Living Ground Cover (LGC): Living ground cover is visually evaluated using a percentage scale (0-99, 99=complete/maximum live ground cover) in spring, summer, and fall. In 2020, mean spring LGC rating of 'OKC3920' (73.2) in Missouri and Mississippi was lower than that of 'TifEagle' (92.8), but not different from that of 'Tifdwarf' (72.2) and 'P18' (70.8). The 2020 mean summer LGC rating of 'OKC3920' (82.2) in California, Indiana, Missouri, and New Mexico was not different from that of 'TifEagle' (86.3) and 'P18' (76.1), but better than that of 'Tifdwarf' (67.3). In the fall of 2020, the mean LGC of 'OKC3920' (70.1) in California, Indiana, and New Mexico was lower than that of 'Tifdwarf' (92.1), 'TifEagle' (88.4), and 'P18' (85.9).

Seedhead Ratings: Seedheads are an undesirable trait for turf, generally considered unsightly, and reduce the turf quality. Seedheads are rated from 1 to 9 with 1 equaling complete seed head coverage and 9 equaling no seedheads. The 2019 NTEP test seedhead data indicated that 'OKC3920' had a seedhead rating averaged over two locations (Indiana and New Mexico) (7.0) similar to that of 'Tifdwarf' (6.0), but smaller than that of 'P18' (9.0) and 'TifEagle' (8.8).

Disease, Insect, and Nematode Responses: No significant damage caused by disease pathogens, insects, or nematodes has been reported for 'OKC3920' in the 2019 NTEP trial. In trials conducted over several years in Stillwater, Oklahoma, 'OKC3920' had similar leaf spot and root-decline or warm-season grass disease severities when compared to other widely used cultivars. Root-knot nematode populations were slightly lower in the multi-year trial suggesting there might be better root-knot nematode tolerance in 'OKC3920'. Other less damaging nematodes had similar populations on all cultivars evaluated.

Tolerance to Commonly Used Herbicides/PGRs: A greenhouse trial was conducted using cone-tainers of 'OKC3920' and 'TifEagle' to evaluate visual injury and turf quality at 3, 7, and 14 day after application of 1× or 2× rates of trinexapac-ethyl, trifloxysulfuron-sodium, sulfentrazone, a mixture of 2,4-D, dicamba, and MCPP. Visual injury was observed for each cultivar under the 2× rate of sulfentrazone, but no differences in visual injury were observed between cultivars for any product or rate. Turf quality scores were reduced by the 2× application of sulfentrazone for each cultivar. The 1× application of sulfentrazone reduced turf quality of 'OKC3920' but not 'TifEagle', although mean turf quality scores for 'OKC3920' were still acceptable (>6).

Major Strengths and Comparative Performance: 'OKC3920' is a new interspecific F1 hybrid turf bermudagrass that has exhibited improved freeze tolerance significantly better than ultradwarf cultivars. It has demonstrated high turfgrass quality as good as ultradwarf cultivars under mowing heights as low as 3.2 mm. It has sufficient establishment characteristics, fine texture, early spring green up, and dark green color. Its ball roll distance approaches that of ultradwarf cultivars. It is recommended for use in putting greens on golf courses and other areas where high quality turfgrass is needed and good management can be practiced in the US transition zone and southern states. 'OKC3920' bermudagrass must be vegetatively propagated due to its infertility.

We claim:

1. A new and distinct Bermudagrass plant named 'OKC3920' substantially as described and illustrated herein.

* * * * *

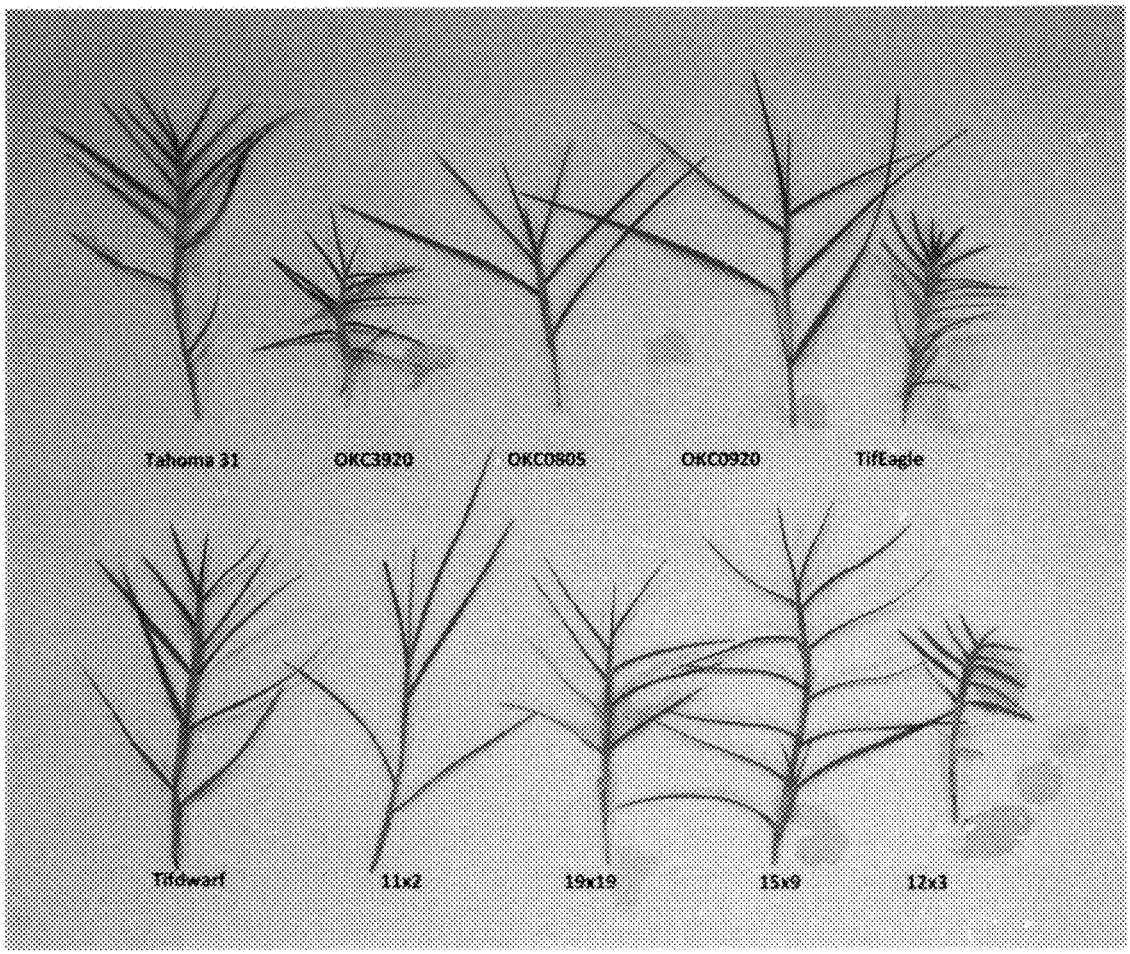
Tahoma 31
OKC3920
OKC0805
OKC0920
TifEagle
TifDwarf
11x2
19x19
15x9
12x3